United States Patent
Grummitt et al.

(10) Patent No.: US 10,006,000 B2
(45) Date of Patent: Jun. 26, 2018

(54) PARTICLE MANIPULATION SYSTEM WITH OUT-OF-PLANE CHANNEL USING AXIAL LIGHT LOSS

(71) Applicants: Daryl Grummitt, Santa Barbara, CA (US); John S. Foster, Santa Barbara, CA (US)

(72) Inventors: Daryl Grummitt, Santa Barbara, CA (US); John S. Foster, Santa Barbara, CA (US)

(73) Assignee: Owl biomedical, Inc., Goleta, CA (US)

(*) Notice: Subject to any disclaimer, the term of this patent is extended or adjusted under 35 U.S.C. 154(b) by 65 days.

(21) Appl. No.: 15/151,518

(22) Filed: May 11, 2016

(65) Prior Publication Data

US 2017/0327783 A1 Nov. 16, 2017

Related U.S. Application Data

(63) Continuation-in-part of application No. 13/998,095, filed on Oct. 1, 2013, now Pat. No. 9,372,144.

(51) Int. Cl.
*G01N 15/14* (2006.01)
*B01L 3/00* (2006.01)
*C12M 1/00* (2006.01)
*G01N 15/10* (2006.01)

(52) U.S. Cl.
CPC .......... *C12M 47/04* (2013.01); *G01N 15/1434* (2013.01); *G01N 15/1459* (2013.01); *G01N 15/1484* (2013.01); *G01N 2015/1081* (2013.01); *G01N 2015/149* (2013.01)

(58) Field of Classification Search
CPC .......... G01N 2001/205; G01N 1/2035; G01N 30/74; G01N 2015/149; G01N 2015/1484
See application file for complete search history.

(56) References Cited

U.S. PATENT DOCUMENTS

| | | | |
|---|---|---|---|
| 5,678,751 A * | 10/1997 | Buchanan | G01N 21/8507 228/124.6 |
| 2001/0055812 A1 | 12/2001 | Mian | |
| 2007/0178529 A1 | 8/2007 | Breidford | |
| 2010/0225913 A1 | 9/2010 | Trainer | |
| 2012/0122084 A1 | 5/2012 | Wagner et al. | |
| 2012/0190105 A1* | 7/2012 | Foster | B01L 3/502761 435/288.7 |
| 2014/0030696 A1* | 1/2014 | Luscher | G01N 15/1404 435/3 |
| 2015/0093817 A1 | 4/2015 | Foster et al. | |

* cited by examiner

*Primary Examiner* — Christopher Adam Hixson
(74) *Attorney, Agent, or Firm* — Jaquelin K. Spong

(57) ABSTRACT

A particle manipulation system uses a MEMS-based, microfabricated particle manipulation device which has an inlet channel, output channels, and a movable member formed on a substrate. The movable member moves parallel to the fabrication plane, as does fluid flowing in the inlet channel. The movable member separates a target particle from the rest of the particles, diverting it into an output channel. The target particles may be identified by a marker-free signal such as axial light loss to identify highly pigmented particles.

13 Claims, 11 Drawing Sheets

PARTICLE MANIPULATION SYSTEM WITH OUT-OF-PLANE CHANNEL USING AXIAL LIGHT LOSS

CROSS REFERENCE TO RELATED APPLICATIONS

This US Patent Application is a continuation-in-part from U.S. patent application Ser. No. 13/998,095, filed Oct. 1, 2013. This application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices may be fabricated on a semiconductor substrate which may manipulate particles passing by the MEMS device in a fluid stream.

In another example, a MEMS devices may be a movable valve, used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to re-sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '899 application) and Ser. No. 13/374,898 (the '898 application) provide further details of other MEMS designs. Each of these patents ('056, '972, '594 and '838) and patent applications ('898 and '899) is hereby incorporated by reference.

SUMMARY

One feature of the MEMS-based microfabricated particle sorting system is that the fluid may be confined to small, microfabricated channels formed in a semiconductor substrate throughout the sorting process. The MEMS device may be a valve which separates one or more target particles from other components of a sample stream. The MEMS device may redirect the particle flow from one channel into another channel, when a signal indicates that a target particle is present. This signal may be photons from a fluorescent tag which is affixed to the target particles and excited by laser illumination in an interrogation region upstream of the MEMS device. Thus, the MEMS device may be a particle or cell sorter operating on a fluid sample confined to a microfabricated fluidic channel, but using detection means similar to a FACS flow cytometer. In particular, the '898 application discloses a microfabricated fluidic valve wherein the inlet channel, sort channel and waste channel all flow in a plane parallel to the fabrication plane of the microfabricated fluidic valve.

A substantial improvement may be made over the prior art devices by having at least one of the microfabricated fluidic channels route the flow out of the plane of fabrication of the microfabricated valve. A valve with such an architecture has the advantage that the pressure resisting the valve movement is minimized when the valve opens or closes, because the movable member is not required to move a column of fluid out of the way. Instead, the fluid containing the non-target particles may move over and under the movable member to reach the waste channel. Furthermore, the force-generating apparatus may be disposed closer to the movable valve, resulting in higher forces and faster actuation speeds. As a result, the time required to open or close the valve may be much shorter than the prior art valve, improving sorting speed and accuracy. The systems and methods disclosed here may describe such a microfabricated particle sorting device with at least one out-of-plane channel.

In the systems and methods disclosed here, a micromechanical particle manipulation device may be formed on a surface of a fabrication substrate, wherein the micromechanical particle manipulation device may include a microfabricated, movable member having a first diverting surface, wherein the movable member moves from a first position to a second position in response to a force applied to the movable member, wherein the motion is substantially in a plane parallel to the surface, a sample inlet channel formed in the substrate and through which a fluid flows, the fluid including at least one target particle and non-target material, wherein the flow in the sample inlet channel is substantially parallel to the surface, and a plurality of output channels into which the microfabricated member diverts the fluid, and wherein the flow in at least one of the output channels is not parallel to the plane, wherein at least one output channel is located directly below at least a portion of the microfabricated diverter over at least a portion of its motion. In one embodiment, The micromechanical particle manipulation device of claim 1, wherein the first diverting surface has a smoothly curved shape which is substantially tangent to the direction of flow in the inlet channel at one point on the shape and substantially tangent to the direction of flow of a first output channel at a second point on the shape, wherein the first diverting surface diverts flow from the inlet channel into the first output channel when the movable member is in the first position, and allows the flow into a second output channel in the second position.

Because of the unique architecture of these systems and methods, new and useful features may be implemented. For example, a particle manipulation system based on markerless signals may be implemented, such as axial light loss (ALL). In ALL, a sort trigger signal is derived from the degree to which the laser light is obscured by a passing particle. Large, pigmented particles such as epithelial cells are effective at absorbing or obscuring light. Accordingly, epithelial cells can be accurately detected and sorted. This technique may enable new therapies involving these cells.

Accordingly, the particle sorting system with light-signal based particle detection, may include a fluid stream containing target particles and non-target material, flowing in a microfabricated channel, an optical light source which emits a beam of light into the channel, a microfabricated particle sorting valve disposed in the channel, a detector which makes measures a marker-less signal as the target particle passes through beam of the light source, and a control mechanism that generates a trigger signal to open the microfabricated particle sorting valve to deflect the target particle from the fluid stream in response to the loss of light.

These and other features and advantages are described in, or are apparent from, the following detailed description.

BRIEF DESCRIPTION OF THE DRAWINGS

Various exemplary details are described with reference to the following figures, wherein.

It should be understood that the drawings are not necessarily to scale, and that like numbers may refer to like features.

DETAILED DESCRIPTION

The system described herein is a particle sorting system which may make use of the microchannel architecture of a MEMS particle manipulation system. More generally, the systems and methods describe a particle manipulation system with an inlet channel and a plurality of output channels, wherein at least one of the plurality of output channels is disposed in a different plane than the inlet channel. This architecture has some significant advantages relative to the prior art.

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as "top," "bottom," "upper," "lower," "left" and "right" are arbitrary, as the device may be constructed and operated in any particular orientation. In particular, it should be understood that the designations "sort" and "waste" are interchangeable, as they only refer to different populations of particles, and which population is called the "target" or "sort" population is arbitrary.

Figure 1:
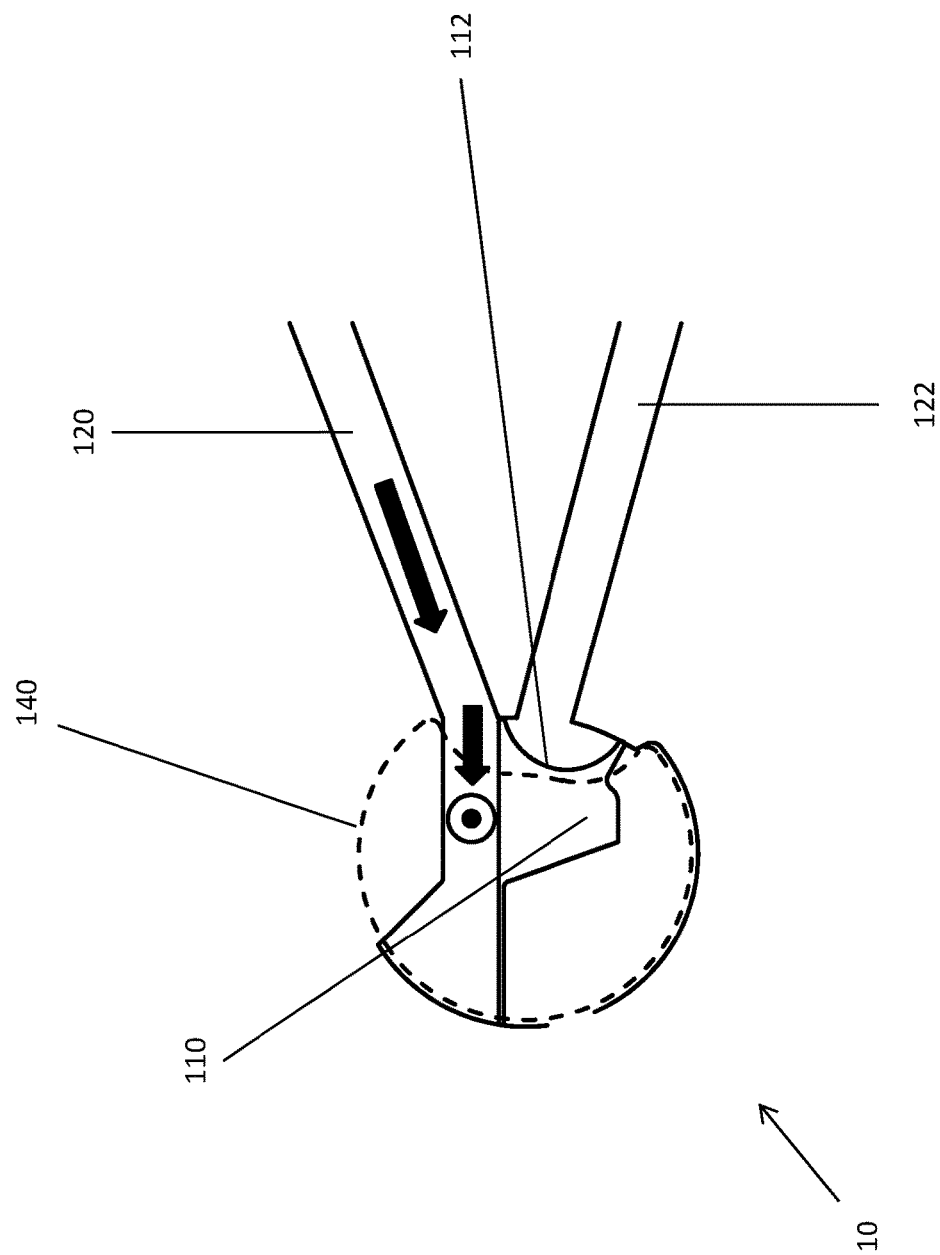
FIG. 1 is a simplified plan view of a microfabricated particle sorting system in the quiescent (no sort) position.

FIG. 1 is an plan view illustration of the novel microfabricated fluidic device 10 in the quiescent (un-actuated) position. The device 10 may include a microfabricated fluidic valve or movable member 110 and a number of microfabricated fluidic channels 120, 122 and 140. The fluidic valve 110 and microfabricated fluidic channels 120, 122 and 140 may be formed in a suitable substrate, such as a silicon substrate, using MEMS lithographic fabrication techniques as described in greater detail below. The fabrication substrate may have a fabrication plane in which the device is formed and in which the movable member 110 moves.

A sample stream may be introduced to the microfabricated fluidic valve 110 by a sample inlet channel 120. The sample stream may contain a mixture of particles, including at least one desired, target particle and a number of other undesired, nontarget particles. The particles may be suspended in a fluid. For example, the target particle may be a biological material such as a stem cell, a cancer cell, a zygote, a protein, a T-cell, a bacteria, a component of blood, a DNA fragment, for example, suspended in a buffer fluid such as saline. The inlet channel 120 may be formed in the same fabrication plane as the valve 110, such that the flow of the fluid is substantially in that plane. The motion of the valve 110 is also within this fabrication plane. The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Details as to this detection mechanism are well known in the literature, and further discussed below with respect to FIG. 12. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an nontarget particle and thus rejected or otherwise disposed of.

With the valve 110 in the position shown, the input stream passes unimpeded to an output orifice and channel 140 which is out of the plane of the inlet channel 120, and thus out of the fabrication plane of the device 10. That is, the flow is from the inlet channel 120 to the output orifice 140, from which it flows substantially vertically, and thus orthogonally to the inlet channel 120. This output orifice 140 leads to an out-of-plane channel that may be perpendicular to the plane of the paper showing FIG. 1, and depicted in the cross sectional views of FIGS. 4a-4c. More generally, the output channel 140 is not parallel to the plane of the inlet channel 120 or sort channel 122, or the fabrication plane of the movable member 110.

The output orifice 140 may be a hole formed in the fabrication substrate, or in a covering substrate that is bonded to the fabrication substrate. A relieved area above and below the sorting valve or movable member 110 allows fluid to flow above and below the movable member 110 to output orifice 140, and shown in more detail in FIGS. 4a-4c. Further, the valve 110 may have a curved diverting surface 112 which can redirect the flow of the input stream into a sort output stream, as described next with respect to FIG. 2. The contour of the orifice 140 may be such that it overlaps some, but not all, of the inlet channel 120 and sort channel 122. By having the contour 140 overlap the inlet channel, and with relieved areas described above, a route exists for the input stream to flow directly into the waste orifice 140 when the movable member or valve 110 is in the un-actuated waste position.

Figure 2:
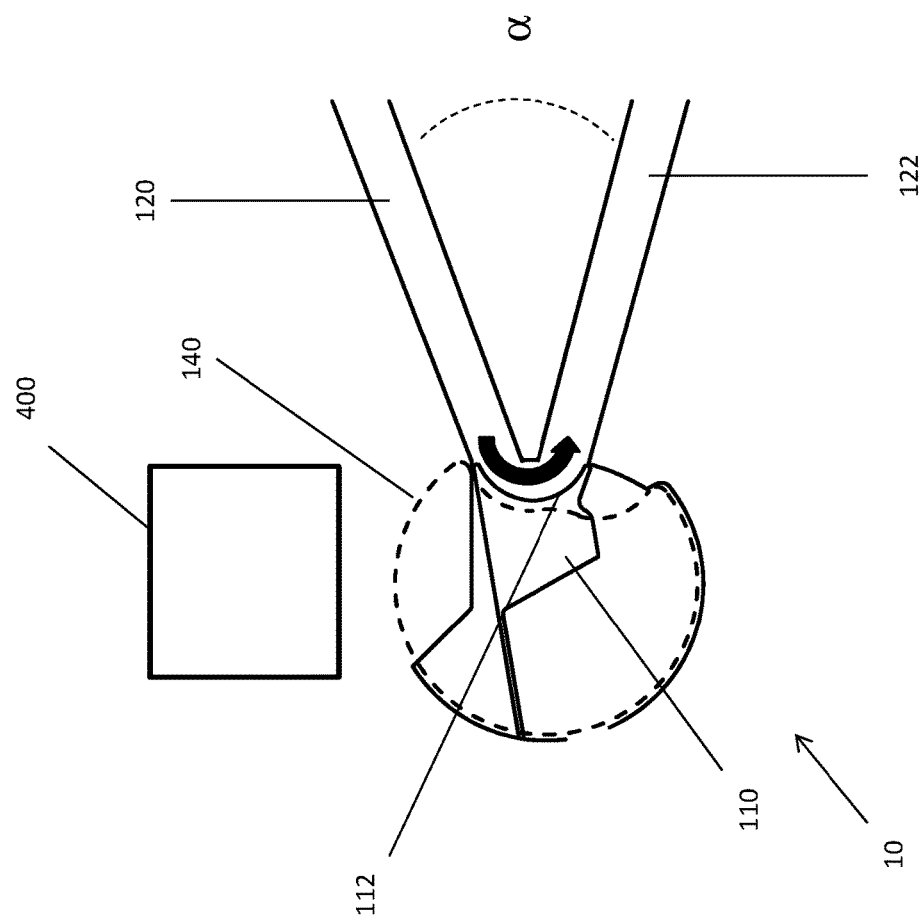
FIG. 2 is a simplified plan view of a microfabricated particle sorting system in the actuated (sort) position.

FIG. 2 is a plan view of the microfabricated device 10 in the actuated position. In this position, the movable member or valve 110 is deflected upward into the position shown in FIG. 2. The diverting surface 112 is a sorting contour which redirects the flow of the inlet channel 120 into the sort output channel 122. The output channel 122 may lie in substantially the same plane as the inlet channel 120, such that the flow within the sort channel 122 is also in substantially the same plane as the flow within the inlet channel 120. There may be an angle α between the inlet channel 120 and the sort channel 122, This angle may be any value up to about 90 degrees. Actuation of movable member 110 may arise from a force from force-generating apparatus 400, shown generically in FIG. 2. In some embodiments, force-generating apparatus may be an electromagnet, however, it should be understood that force-generating apparatus may also be electrostatic, piezoelectric, or some other means to exert a force on movable member 110, causing it to move from a first position (FIG. 1) to a second position (FIG. 2).

More generally, the micromechanical particle manipulation device shown in FIGS. 1 and 2 may be formed on a surface of a fabrication substrate, wherein the micromechanical particle manipulation device may include a microfabricated, movable member 110 having a first diverting surface 112, wherein the movable member 110 moves from a first position to a second position in response to a force applied to the movable member, wherein the motion is substantially in a plane parallel to the surface, a sample inlet channel 120 formed in the substrate and through which a fluid flows, the fluid including one or more target particles and non-target material, wherein the flow in the sample inlet channel is substantially parallel to the surface, and a plurality of output channels 122, 140 into which the microfabricated member diverts the fluid, and wherein the flow in at least one of the output channels 140 is not parallel to the plane, and wherein at least one output channel 140 is located directly below at least a portion of the movable member 110 over at least a portion of its motion.

In one embodiment, the diverting surface 112 may be nearly tangent to the input flow direction as well as the sort output flow direction, and the slope may vary smoothly between these tangent lines. In this embodiment, the moving mass of the stream has a momentum which is smoothly shifted from the input direction to the output direction, and thus if the target particles are biological cells, a minimum of force is delivered to the particles. As shown in FIGS. 1 and 2, the micromechanical particle manipulation device 10 has a first diverting surface 112 with a smoothly curved shape, wherein the surface which is substantially tangent to the direction of flow in the sample inlet channel at one point on the shape and substantially tangent to the direction of flow of a first output channel at a second point on the shape, wherein the first diverting surface diverts flow from the sample inlet channel into the first output channel when the movable member 110 is in the first position, and allows the flow into a second output channel in the second position.

In other embodiments, the overall shape of the diverter 112 may be circular, triangular, trapezoidal, parabolic, or v-shaped for example, but the diverter serves in all cases to direct the flow from the inlet channel to another channel.

It should be understood that although channel 122 is referred to as the "sort channel" and orifice 140 is referred to as the "waste orifice", these terms can be interchanged such that the sort stream is directed into the waste orifice 140 and the waste stream is directed into channel 122, without any loss of generality. Similarly, the "inlet channel" 120 and "sort channel" 122 may be reversed. The terms used to designate the three channels are arbitrary, but the inlet stream may be diverted by the valve 110 into either of two separate directions, at least one of which does not lie in the same plane as the other two. The term "substantially" when used in reference to an angular direction, i.e. substantially tangent or substantially vertical, should be understood to mean within 15 degrees of the referenced direction. For example, "substantially orthogonal" to a line should be understood to mean from about 75 degrees to about 105 degrees from the line.

Figure 3B:
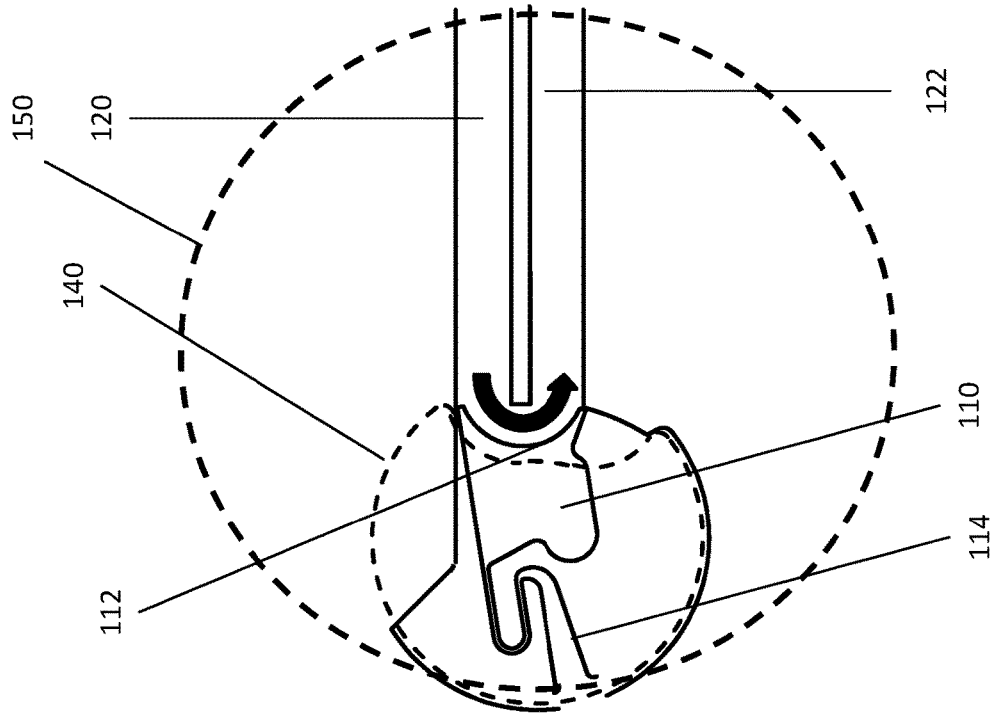
FIG. 3b is a simplified illustration of a microfabricated particle sorting system showing the field of view of the detector, with the microfluidic valve in the actuated (sort) position.
Figure 3A:
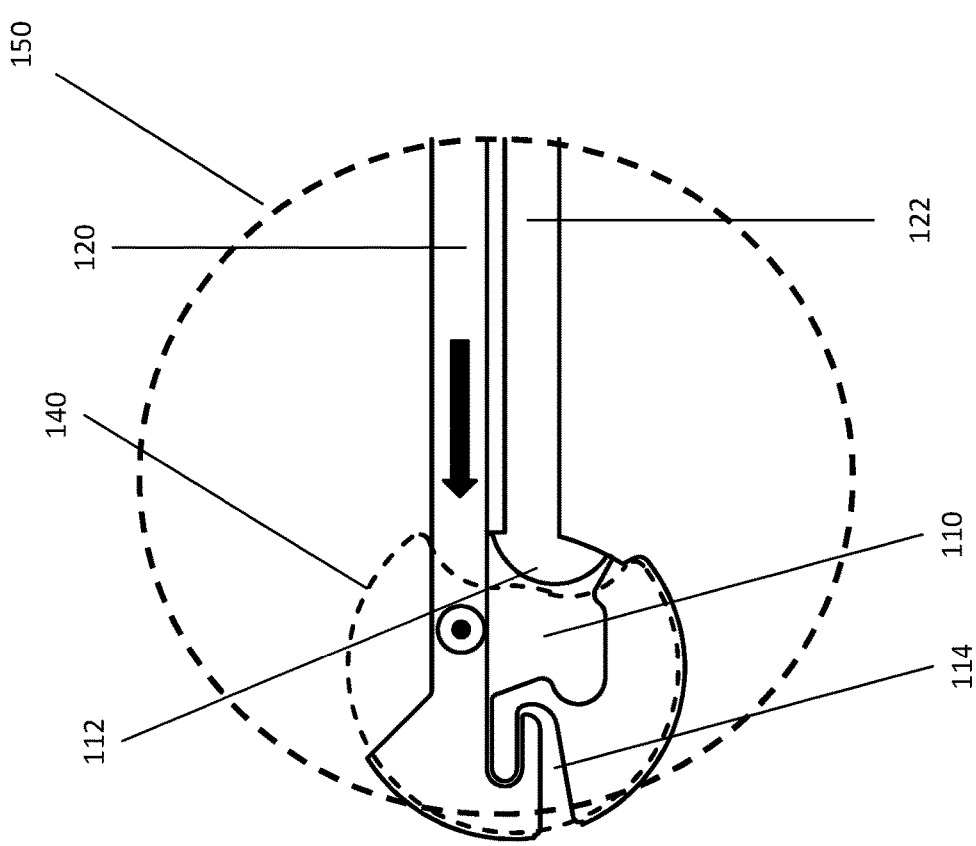
FIG. 3a is a simplified plan view of a microfabricated particle sorting system showing the field of view of the detector, with the microfluidic valve in the quiescent (no sort) position.

FIGS. 3a and 3b illustrate an embodiment wherein the angle α between the inlet channel 120 and the sort channel 122 is approximately zero degrees. Accordingly, the sort channel 122 is essentially antiparallel to the inlet channel 120, such that the flow is from right to left in the inlet channel 120. With valve 110 in the un-actuated, quiescent position shown in FIG. 3a, the inlet stream flows straight to the waste orifice 140 and vertically out of the device 10.

In FIG. 3b, the valve 110 is in the actuated, sort position. In this position, the flow is turned around by the diverting surface 112 of the valve 110 and into the antiparallel sort channel 122. This configuration may have an advantage in that the field of view of the detector 150 covers both the inlet channel 120 and the sort channel 122. Thus a single set of detection optics may be used to detect the passage of a target particle through the respective channels. It may also be advantageous to minimize the distance between the detection region and the valve 110, in order to minimize the timing uncertainty in the opening and closing of the valve.

Figure 4A:
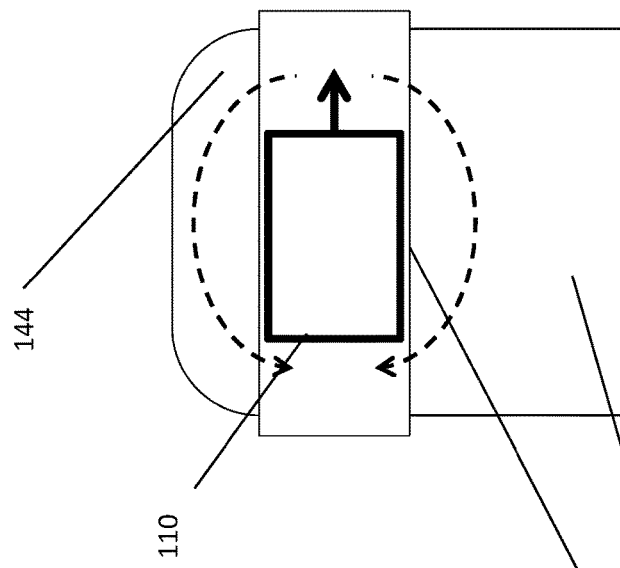
FIG. 4a is a simplified cross sectional view of a microfabricated particle sorting system in the actuated (sort) position, showing the flow of the sample stream into the sort channel which is in the same plane as the inlet channel.
Figure 4B:
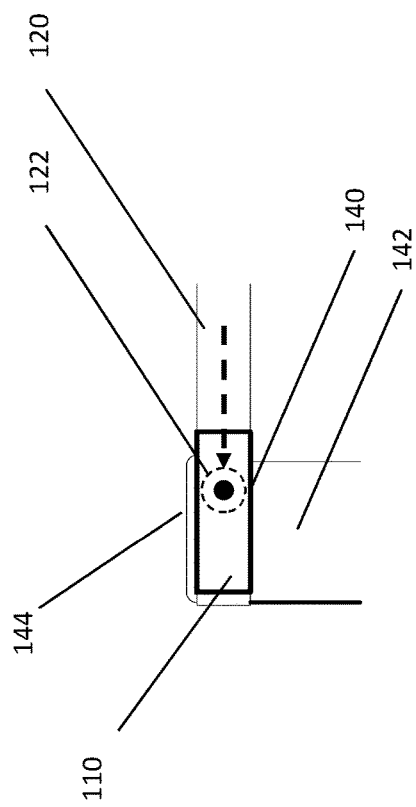
FIG. 4b is a simplified cross sectional view of a microfabricated particle sorting system in the quiescent (no sort) position, showing the flow of the sample stream into the waste channel which is not in the same plane as the inlet channel.
Figure 4C:
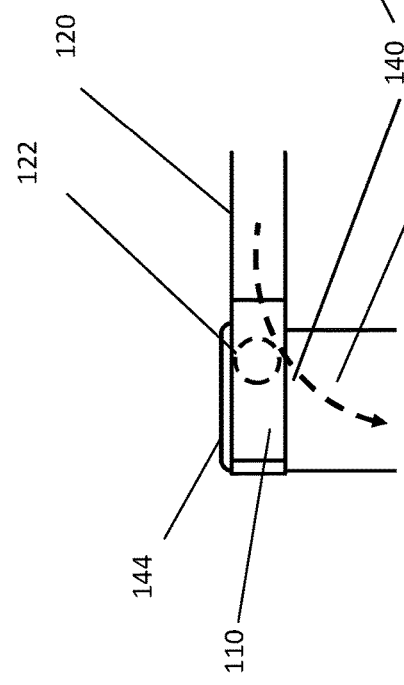
FIG. 4c is a simplified cross sectional view of a microfabricated particle sorting system in the quiescent (no sort) position, showing the flow of the sample stream into the waste channel which is not in the same plane as the inlet channel, wherein the sample stream flows around the top and the bottom of the diverter.

The movable member or valve 110 may be attached to the substrate with a flexible spring 114. The spring may be a narrow isthmus of substrate material. In the example set forth above, the substrate material may be single crystal silicon, which is known for its outstanding mechanical properties, such as its strength, low residual stress and resistance to creep. With proper doping, the material can also be made to be sufficiently conductive so as to avoid charge build up on any portion of the device, which might otherwise interfere with its movement. The spring may have a serpentine shape as shown, having a width of about 1 micron to about 10 microns and a spring constant of between about 10 N/m and 100 N/m, and preferably about 40 N/m FIGS. 4a, 4b, 4c are cross sectional views illustrating the operation of the out-of-plane waste channel 140. FIG. 4c is slightly enlarged relative to FIGS. 4a and 4b, in order to show detail of the flow around the movable member 110 and into the waste channel 142 through waste orifice 140. In this embodiment, the waste channel 142 is vertical, substantially orthogonal to the inlet stream 120 and sort stream 122. It should be understood that other embodiments are possible other than orthogonal, but in any event, the flow into waste channel 142 is out of the plane of the flow in the inlet channel 120 and/or sort channel 122. As shown in FIG. 4a, with the valve in the sort, actuated position, the inlet stream and target particle may flow into the sort stream, which in FIG. 4a is out of the paper, and the waste orifice 140 is largely, though not completely, blocked by the movable member 110. The area 144 (shown more clearly in FIG. 4c) on top of the valve or movable member 110 may be relieved to provide clearance for this flow.

When the valve or movable member 110 is un-actuated as in FIG. 4b, the flow of the inlet channel 120 may flow directly into the waste channel 142 by going over, around or by the movable member or valve 110. The area 144 on top of the valve or movable member 110 may be relieved to provide clearance for this flow. The relieved area 144 is shown in greater detail in the enlarged FIG. 4c. Thus when the movable member is un-actuated, the flow will be sent directly to the waste channel. When the movable member is actuated, most of the fluid will be directed to the sort channel, although liquid may still flow over and under the movable member.

Thus, the purpose of providing flow both under and over the movable member 110 is to reduce the fluid pressure produced by the actuator motion in the region behind the valve or movable member 110. In other words, the purpose is to provide as short a path as possible between the high pressure region in front of the valve 110 and the low pressure region behind the valve. This allows the valve to operate with little pressure resisting its motion. As a result, the movable valve 110 shown in FIGS. 1-4c may be substantially faster than valves which have all channels disposed in the same plane.

Another advantage of the vertical waste channel 142 is that by positioning it directly underneath a stationary permeable feature 130 and movable permeable feature 116, the magnetic gap between the permeable features 116 and 130 can be narrower than if the fluidic channel went between them. The narrower gap enables higher forces and thus faster actuation compared to prior art designs. A description of the magnetic components and the magnetic actuation mechanism will be given next, and the advantages of the out-of-plane channel architecture will be apparent.

Figure 5:
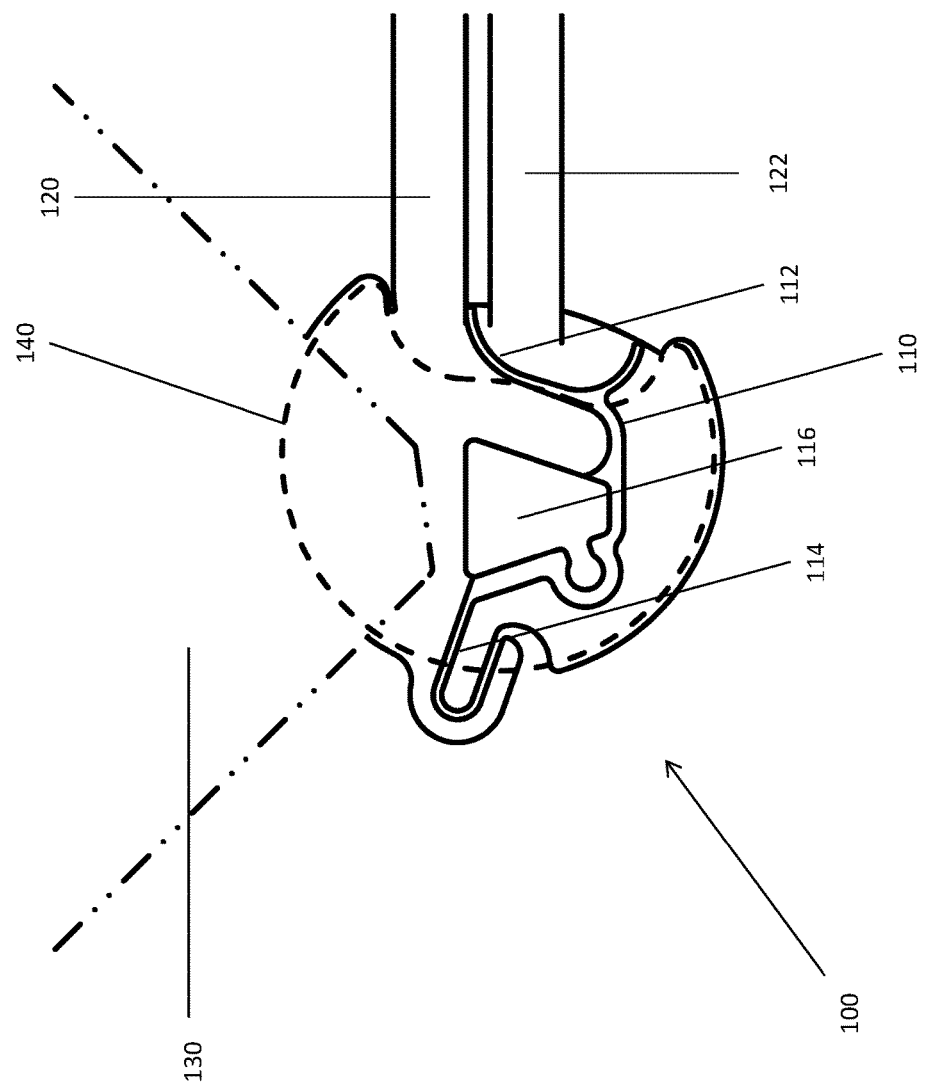
FIG. 5 is a simplified plan view of a microfabricated particle sorting system in the quiescent (no sort) position, showing the stationary magnetically permeable feature.

FIG. 5 is a plan view of another exemplary embodiment of device 100 of the device 10, showing the disposition of a stationary permeable feature 130 and further detail of the movable member 110. In this embodiment, the movable member 110 may include the diverting surface 112, the flexible hinge or spring 114, and a separate area 116 circumscribed but inside the line corresponding to movable member 110. This area 116 may be inlaid with a permeable magnetic material such as nickel-iron permalloy, and may function as described further below.

A magnetically permeable material should be understood to mean any material which is capable of supporting the formation of a magnetic field within itself. In other words, the permeability of a material is the degree of magnetization that the material obtains in response to an applied magnetic field.

The terms "permeable material" or "material with high magnetic permeability" as used herein should be understood to be a material with a permeability which is large compared to the permeability of air or vacuum. That is, a permeable material or material with high magnetic permeability is a material with a relative permeability (compared to air or vacuum) of at least about 100, that is, 100 times the permeability of air or vacuum which is about $1.26 \times 10^{-6}$ $H \cdot m^{-1}$. There are many examples of permeable materials, including chromium (Cr), cobalt (Co), nickel (Ni) and iron (Fe) alloys. One popular permeable material is known as Permalloy, which has a composition of between about 60% and about 90% Ni and 40% and 10% iron. The most common composition is 80% Ni and 20% Fe, which has a relative permeability of about 8,000.

It is well known from magnetostatics that permeable materials are drawn into areas wherein the lines of magnetic flux are concentrated, in order to lower the reluctance of the path provided by the permeable material to the flux. Accordingly, a gradient in the magnetic field urges the motion of the movable member 110 because of the presence of inlaid permeable material 116, towards areas having a high concentration of magnetic flux. That is, the movable member 110 with inlaid permeable material 116 will be drawn in the direction of positive gradient in magnetic flux.

Figure 6:
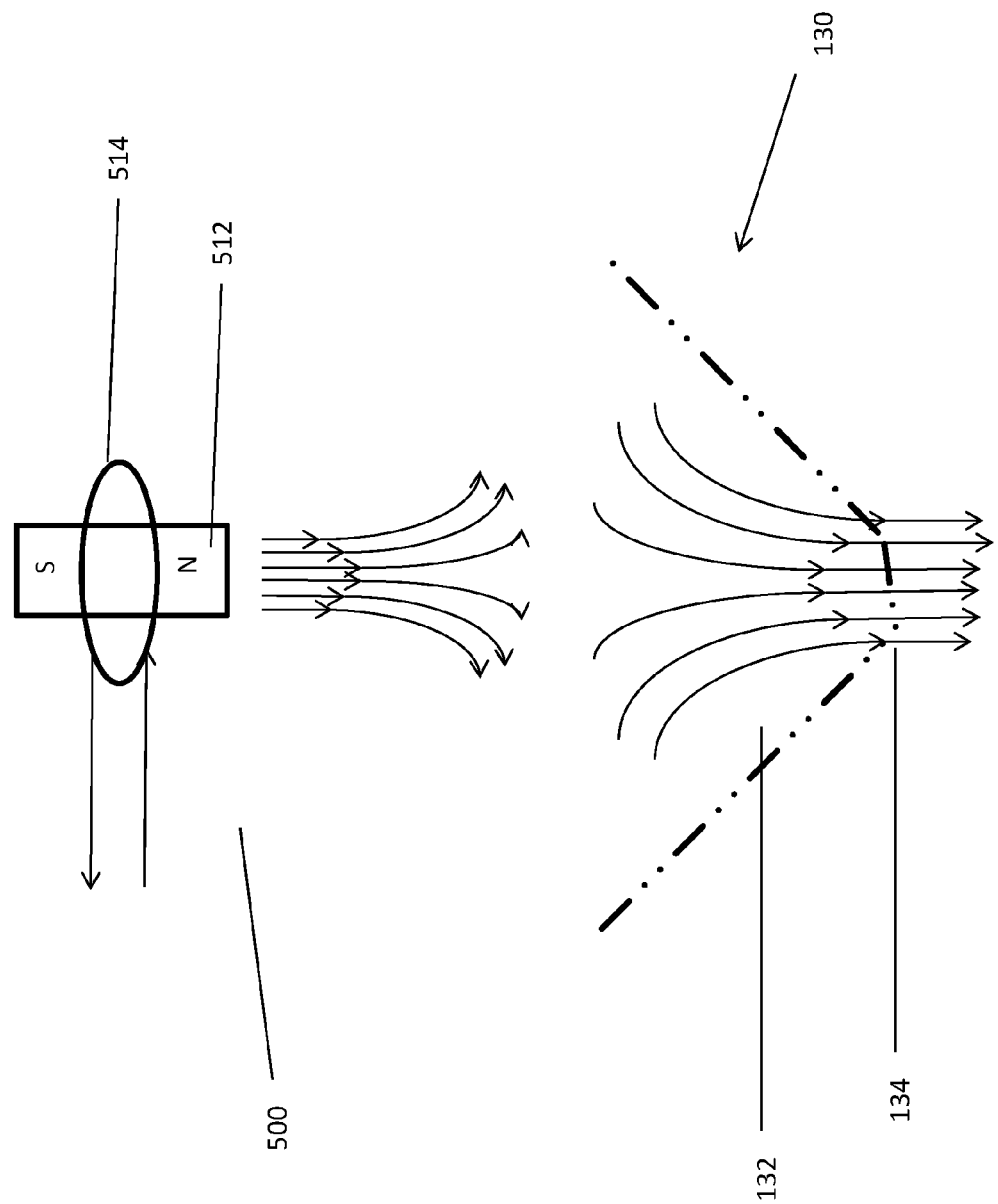
FIG. 6 is a plan view of the actuation mechanism for the microfabricated particle sorting system, showing the functioning of the external magnetic field in combination with the stationary magnetically permeable feature.
Figure 7:
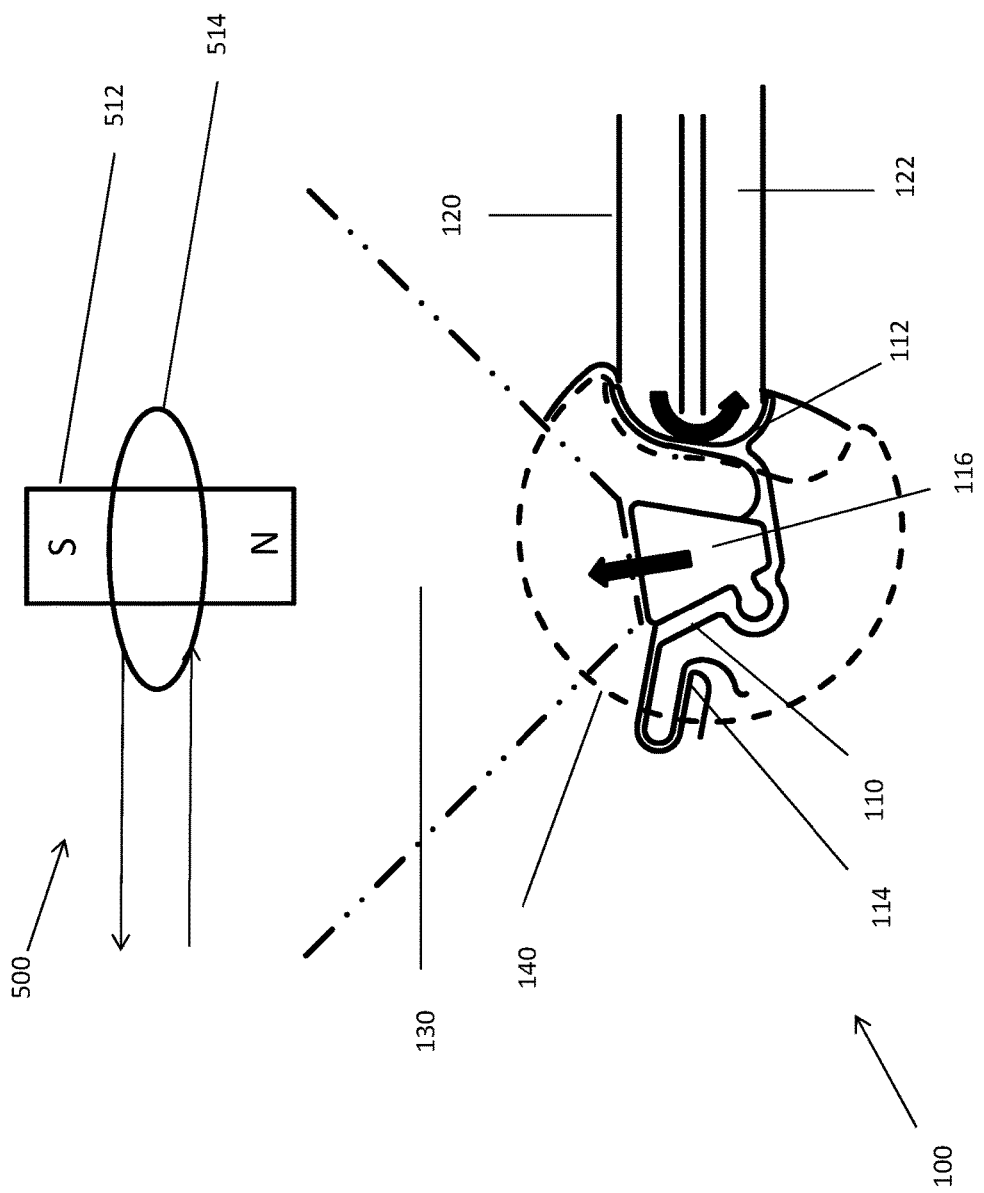
FIG. 7 is a plan view of the actuation mechanism for the microfabricated particle sorting system, showing the functioning of the external magnetic field in combination with the stationary magnetically permeable feature, in the actuated (sort) position.

An external source of magnetic field lines of flux may be provided outside the device 100, as shown in FIG. 6. This source may be an electromagnet 500. The electromagnet 500 may include a permeable core 512 around which a conductor 514 is wound. The wound conductor or coil 514 and core 512 generate a magnetic field which exits the pole of the magnet, diverges, and returns to the opposite pole, as is well known from electromagnetism. Accordingly, the movable member 110 is generally drawn toward the pole of the electromagnet 500 as shown in FIG. 7.

However, the performance of the device 100 can be improved by the use of a stationary permeable feature 130. The term "stationary feature" should be understood to mean a feature which is affixed to the substrate and does not move relative to the substrate, unlike movable member or valve 110. A stationary permeable feature 130 may be shaped to collect these diverging lines of flux and refocus them in an area directly adjacent to the movable member 110 with inlaid permeable material. The stationary permeable feature may have an expansive region 132 with a narrower throat 134. The lines of flux are collected in the expansive region 132 and focused into and out of the narrow throat area 134. Accordingly, the density of flux lines in the throat area 134 is substantially higher than it would be in the absence of the stationary permeable feature 130. Thus, use of the stationary permeable feature 130 though optional, allows a higher force, faster actuation, and reduces the need for the electromagnet 500 to be in close proximity to the device 10. From the narrow throat area 134, the field lines exit the permeable material and return to the opposite magnetic pole of the external source 500. But because of the high concentration of field lines in throat area 134, the permeable material 116 inlaid into movable member 110 may be drawn toward the stationary permeable feature 130, bringing the rest of movable member with it.

When the electromagnet is quiescent, and no current is being supplied to coil 514, the restoring force of spring 114 causes the movable member 110 to be in the "closed" or "waste" position. In this position, the inlet stream passes unimpeded through the device 100 to the waste channel 140. This position is shown in FIG. 5. When the electromagnet 500 is activated, and a current is applied through coil 514, a magnetic field arises in the core 512 and exits the pole of the core 512. These lines of flux are collected and focused by the stationary permeable feature 130 and focused in the region directly adjacent to the throat 134. As mentioned previously, the permeable portion 116 of the movable member 110 is drawn toward the throat 134, thus moving the movable member 110 and diverting surface 112 such that the inlet stream in inlet channel 120 is redirected to the output or sort channel 122. This position is shown in FIG. 7.

Permalloy may be used to create the permeable features 116 and 130, although it should be understood that other permeable materials may also be used. Permalloy is a well known material that lends itself to MEMS lithographic fabrication techniques. A method for making the permeable features 116 and 130 is described further below.

As mentioned previously, having the waste channel 140 and 142 directly beneath the movable member or valve 110 allows the movable permeable feature 116 to be disposed much closer to the stationary permeable feature 130. If instead the waste channel were in the same plane, this gap would have to be at least large enough to accommodate the waste channel, along with associated tolerances. As a result, actuation forces are higher and valve opening and closing times are much shorter. This in turn corresponds to either faster sorting or better sorting accuracy, or both.

With the use of the electromagnetic actuation technique described above, actuation times on the order of 10 microseconds can be realized. Accordingly, the particle sorting device 1 is capable of sorting particles at rates in excess of 50 kHz or higher, assuming 10 microseconds required to pull the actuator in, and 10 microseconds required to return it to the as-manufactured position.

The microfabricated particle sorting system is capable of a variety of operating modes such as laser induced florescence, side scatter and axial light loss (ALL). Each of these optical detection techniques may be best suited to one or another application, such as detecting cellular markers, detecting a certain variety of cell populations, such as T cells or B cells. Many if not all of these techniques include that attachment or conjugation of a fluorescent marker onto the cell of interest, by applying a molecule which has an antibody conjugated to a fluorescent moiety. The antibody attaches to a target particle having the proper antigen displayed on its surface, thereby marking that cell as a target cell. When the target cell passes through the laser interrogation region 170, it is irradiated by a light source operating at a wavelength so as to excite the moiety on the tagged particle. The fluorescent moiety then emits a fluorescent photon which is detected. The target cell may then be separated based on the presence of this fluorescent signal. The use of an antibody/fluorescent tag is known as sorting according to a cellular marker.

In contrast to this technique, the method disclosed here is based on a marker-less effect. A "markerless effect" should be understood to be an effect not related to a cellular antigen or fluorescent signal. Instead, it may be related to the optical properties of the particle itself. A markerless signal may include, therefore, opacity, granularity, shape, size, translucence and pigmentation. A sort signal may be generated based on the presence or absence of this markerless effect. Axial light loss (ALL) is one example of such a markerless effect, as described below.

For the axial light loss (ALL) technique, the microfabricated cell sorter is configured to detect the passage of generally opaque cells. The light source and detector are both orthogonal to the direction of fluid flow in the microchannel. Some particles may be more effective than other particles in absorbing or scattering the incident light. For example, transparent particle interfere relatively little with the incident light, whereas pigmented particles may interfere more completely with the incident light. These highly pigmented cells may be, for example, epithelial cells, skin cell or other relatively opaque types of particles. The light source and detector are generally collinear and at least substantially parallel, in ALL, and the reflected light is separated from incident light by a beamsplitting reflector.

Accordingly, a particle sorting device 1 with light-signal based particle detection is disclosed, comprising a fluid stream containing target particles and non-target material, flowing in a microfabricated channel, an optical light source which emits a beam of light into the channel, a microfabricated particle sorting valve disposed in the channel, a detector which makes measures a markerless effect as the target particle passes through beam of the light source and emits a sort signal, and a control mechanism that generates a trigger signal to open the microfabricated particle sorting valve to deflect the target particle from the fluid stream in response to the sort signal. Some embodiments of the particle sorting device may use axial light loss as the markerless effect, where in the axial light loss may be a reduction in detected axial light due to the obscuring of the light by a passing particle. In some embodiments, the target particle may comprise a pigmented cell.

Figure 8:
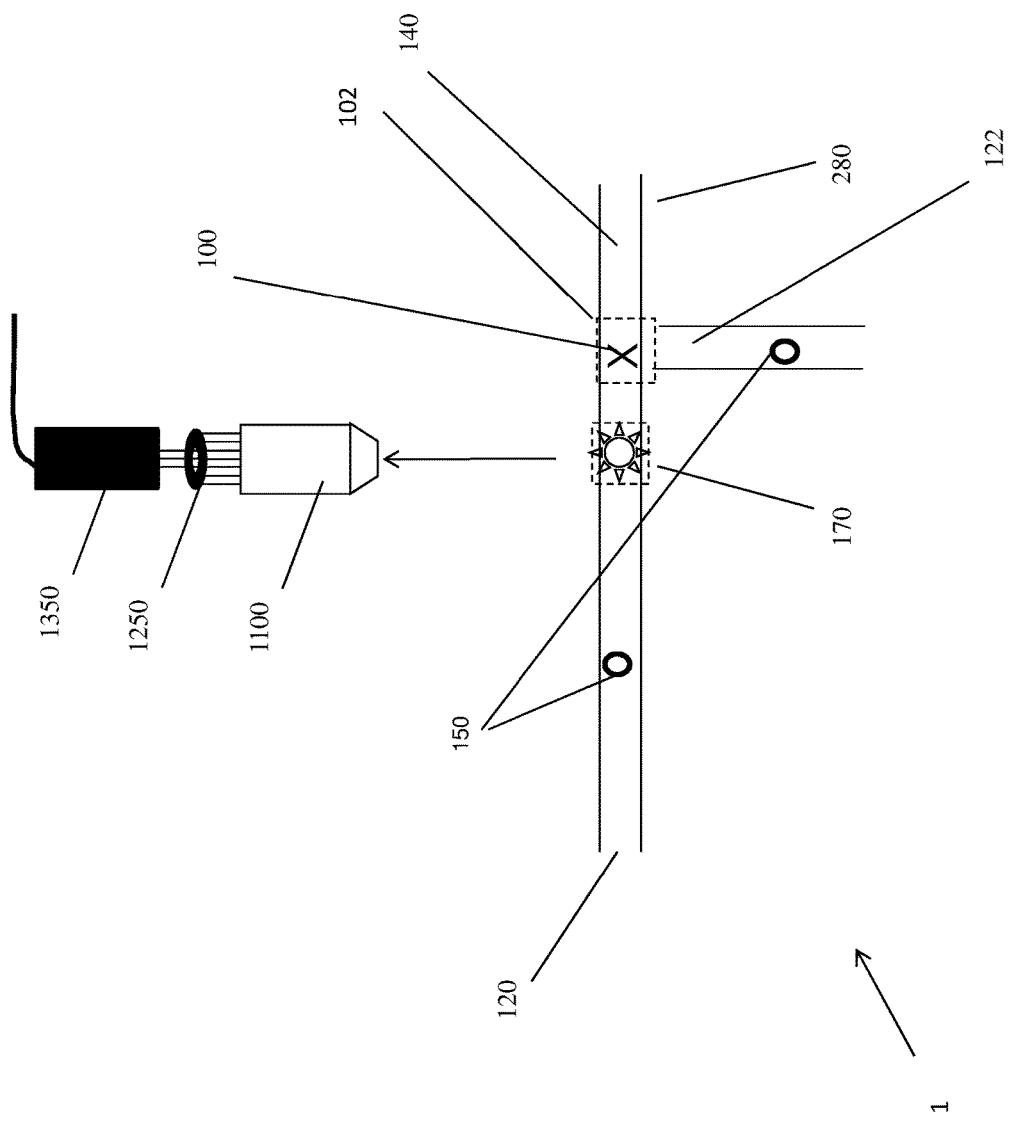
FIG. 8 is a schematic plan view of a microfabricated particle sorting system, using axial light loss.

The microfabricated particle sorting system may be adapted as shown in FIG. 8. FIG. 8 is a simplified schematic view of a microfabricated particle sorting device 1 which is operating in (ALL) mode. In this mode, the microfabricated particle sorting system may measure the relative obscuring of an incident beam of light by the passage of an opaque particle, such as a pigmented cell.

Shown in FIG. 8 is microfabricated particle sorting device 1, which may include is a sample input channel 120 which contains a sample fluid. Suspended in the sample fluid or a plurality of target particles 150, as well as non-target material. The sample fluid flows into input channel 120 past the laser interrogation region 170 and to the microfabricated valve 100. The valve may be of the type described above, wherein the waste channel is substantially orthogonal to the input and sort channels.

The valve 100 may divert target particles into a sort channel 122, if a particular characteristic is detected in the laser interrogation region 170. If the characteristic is not detected, the sample fluid does not contain the particle target and this sample fluid is allowed to pass into the waste channel 140. Although the waste channel 140 is shown in the plane of the paper in FIG. 8, it should be understood that this is for ease of depiction, and that waste channel 140 may be orthogonal to the plane of the paper, as was previously described with respect to FIGS. 1 through 7.

Thus, the valve and movable member 100 as described above may be used in the particle sorting device 1 of FIG. 8. In one embodiment, the microfabricated particle sorting valve comprises: a microfabricated, movable member formed on the substrate, and having a first diverting surface, wherein the movable member moves from a first position to a second position in response to a force applied to the movable member, wherein the motion is substantially in a plane parallel to the surface of the substrate, a sample inlet channel formed in the substrate and through which a fluid flows, the fluid including at least one target particle and non-target material, wherein the flow in the sample inlet channel is substantially parallel to the surface, a plurality of output channels into which the microfabricated member diverts the fluid, and wherein the flow in at least one of the output channels is substantially orthogonal to the plane, and wherein at least one output channel is located directly below at least a portion of the microfabricated member over at least a portion of its motion.

In some embodiments, the plurality of output channels of the microfabricated particle sorting valve may comprise a sort channel and a waste channel, wherein flow in the sort channel is substantially antiparallel to flow in the sample inlet channel, and wherein flow in the waste channel is substantially orthogonal to flow in the sample inlet channel and the sort channel. In other embodiments, the particle sorting device may further comprise a first permeable magnetic material inlaid in the movable member, a first stationary permeable magnetic feature disposed on the substrate, and a first source of magnetic flux external to the movable member and substrate on which the movable member is formed. The movable member moves from the first position to the second position when the source of magnetic flux is activated.

An optical source 1350 may be positioned above the substrate on which the microfabricated sorting system is formed. Although the laser source 1350 as shown in the same plane as the paper and the simple input channel 120 and the sort channel 122, it should be understood that this is for ease of depiction only, and that instead the source 170 maybe oriented orthogonal to the plane of the fluid channels. This configuration is shown more clearly in FIG. 9. In any case, light source 1350 may emit radiation which is passed through a beamsplitting reflector 1250 and through an objective lens 1100. The beam then impinges on the microfabricated channel 120. The light may pass through the fluid and be reflected off the back of the channel, returning back through the optical system 1100, 1250 and 1350, described above.

The beam splitting reflector 1250 may separate the incoming light from the outgoing, reflected light. Accordingly, the optical light source and detector may be substantially parallel, and wherein incident light from the light source is reflected from a back wall of the channel, and wherein the reflected light is separated from incident light by a beam-splitting reflector. "Substantially parallel" should be understood to mean that the optical axis of the light source is within about 10 degrees of parallel to the optical axis of the detector system. These optical axes are shown as a plurality of parallel lines in FIG. 11.

Figure 9:
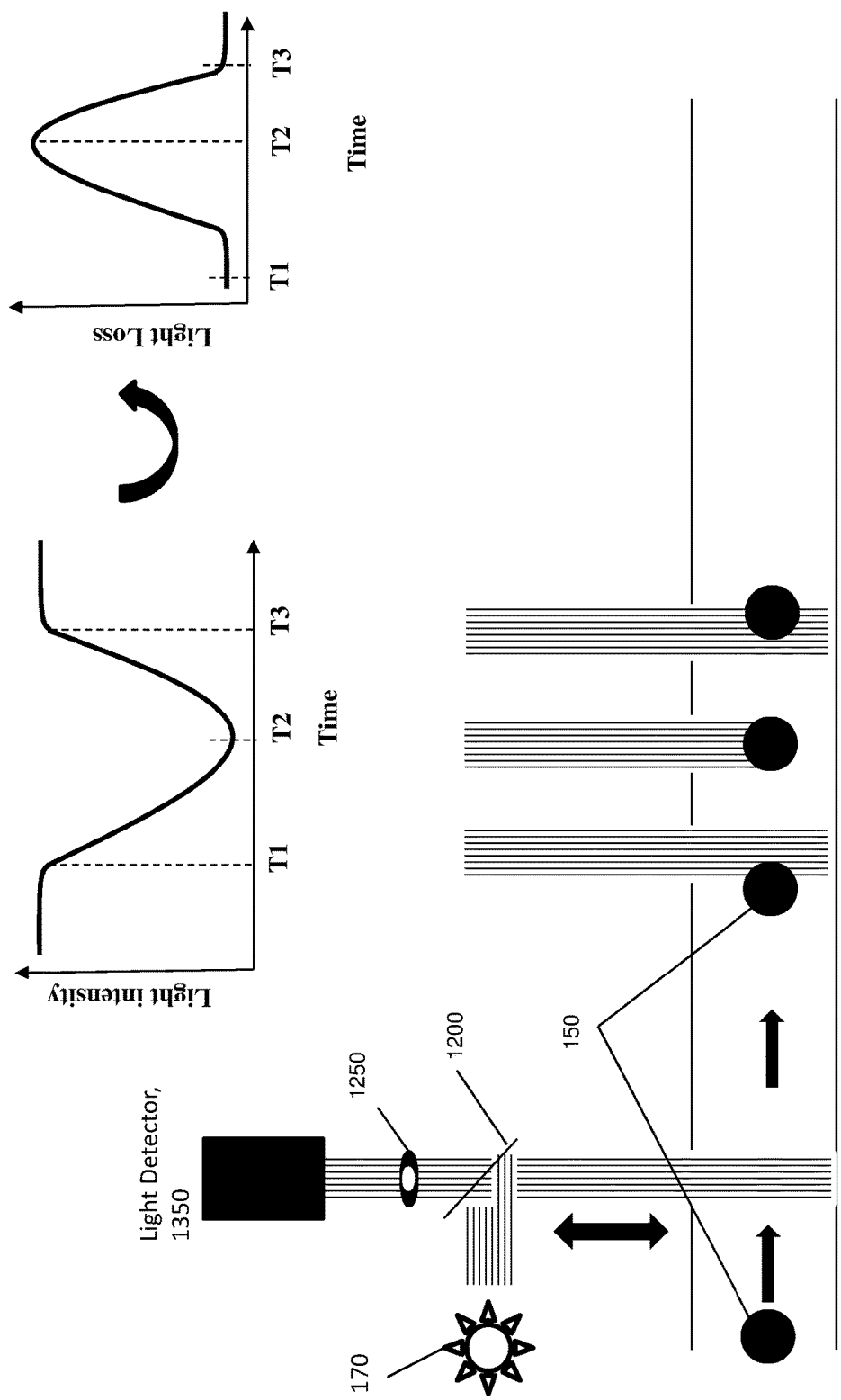
FIG. 9 is a schematic diagram of the technique for sorting using light loss for light-obscuring particles.

FIG. 9 is a diagrammatic view of the ALL detection methodology. As before, target particle 150 is shown suspended in a sample fluid which is passing through input microchannel 120. At one point in the microchannel, the target particle 150 traverses the beam of light emitted from a light source 170. Light source 170 units radiation which is reflected off of the beam splitter 1200, and directed into the microchannel 120. This radiation traverses the fluid in the channel, and bounces off the rear of the channel, back up to the beam splitter 1200 through the beam splitter through a lens 1215 and to the detector 1350. Accordingly as target particle 150 traverses through the beam from light source 170, it partially obscures both the incoming, and outgoing light. As a result the signal from the detector begins at a reference level shown in the first insert of FIG. 9 and is then diminished as the target particle passes through the beam. At time T=T0, the target particle just begins to obscure the beam of light. At a later time T=T1, the target particle is fully with in the envelope of the beam, and the obscuring of the light from the particle is in at a maximum. At a time T=T2, the particle is exiting the beam of light and the light intensity recovers to its original level.

As used in the detection methodology, this light lost signal is inverted, so that the magnitude of the lost light is displayed as a positive number. This is shown in the second insert of FIG. 9. Accordingly, at T=T1, the particle just enters the radiation area, but time T=T2, the particle is obscuring the radiation at a maximum. At time T=T3, the particle is just exiting the beam of light.

Accordingly, the amplitude of the light loss is indicative of the effectiveness with which the passing particle 150 obscures the incoming, and outgoing beam of light from source 170. Some target particles are relatively transparent, and therefore obscure the light minimally. Other particles are relatively opaque and obscure the light quite effectively. Such target particles may be highly pigmented cells, for example epithelial cells, and those containing melanin.

The ability to separate such highly pigmented cells may be a critical improvement in the treatment of many disorders. Just one example is the treatment of macular degeneration, in which the retinal pigment epithelium stops delivering nutrients to the rods and cones of the eye, resulting in a loss of central vision. Some researchers are using induced pluripotent stem (iPS) cells, tissue-specific cells (usually skin cells, but sometimes other tissue cells) that are reprogrammed in the lab to behave like embryonic stem cells—to grow rods and cones or RPE cells. The process of isolating sufficient numbers of stem cells is extremely laborious and time consuming. The microfabricated particle sorting system described here may revolutionize treatment of this disorder, by speeding treatment from months to hours. The stem cells can be separated at a rapid rate using the system described here. The sorting mechanism is so gentle that very high viability numbers, routinely in excess of 90%, can be achieved in the sorted cell product.

Figure 10:
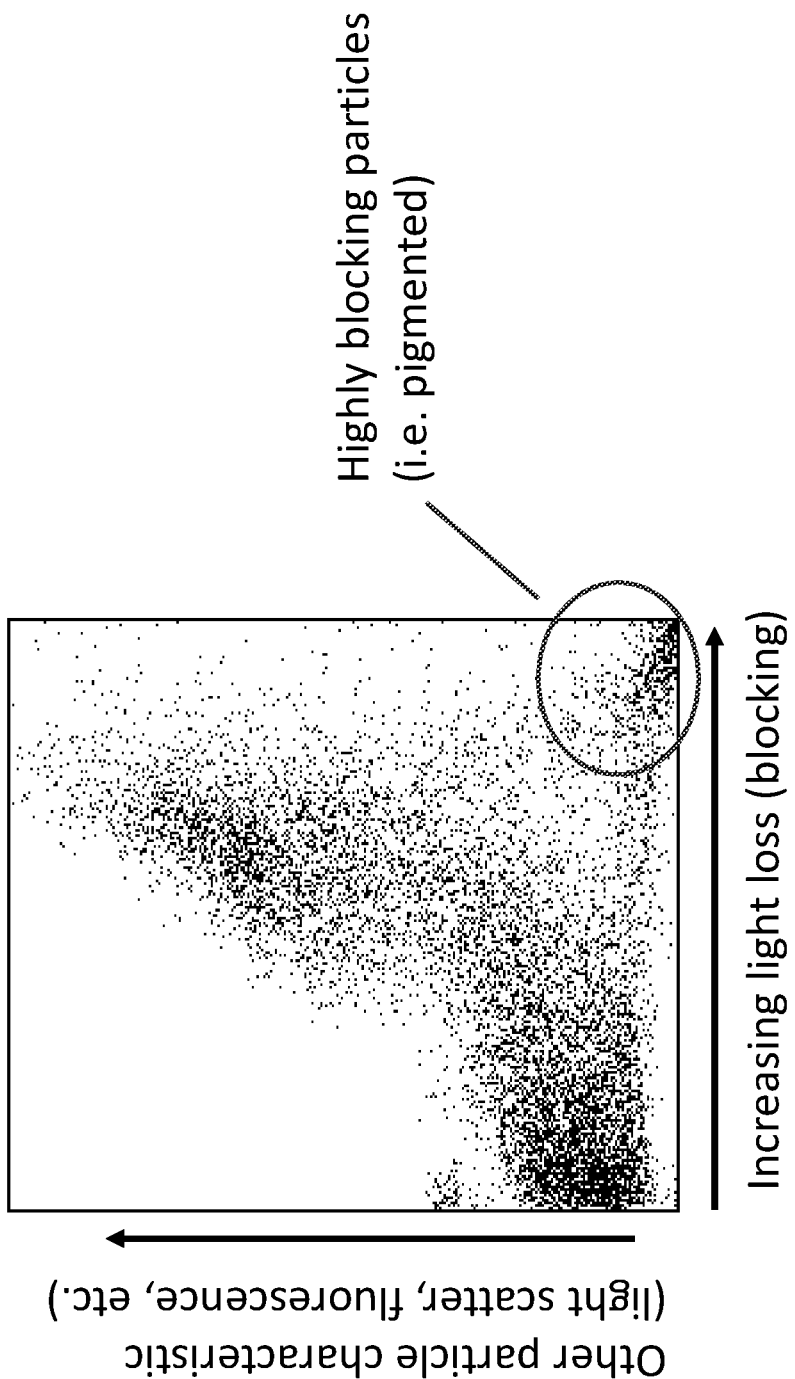
FIG. 10 is a plot of data showing the effectiveness of the ALL parameter in sorting a pigmented particle.

FIG. 10 is a bivariant data plot showing the light loss caused by a variety of particles passing through the beam of light, and a fluid stream. On the vertical axis is one sorting parameter such as side scatter or fluorescence. On the horizontal axis is the axial light loss (ALL) signal. The identity of each particle in the plot was confirmed by other methods (flow cytometry). As shown in FIG. 10, the highly blocking, pigmented particles such as RPEs are tightly clustered in the lower right hand corner. This suggests that ALL is an effective sorting parameter using the microfabricated particle manipulation device 10 or 100. And in fact, sorting routines using the microfabricated particle manipulation device 10 or 100 and sorting on the ALL parameter as shown in FIG. 10 have produced purified samples comprising millions of epithelial stem cells with purities in excess of 90% viabilities in excess of 90% all within a matter of a few hours.

As can be seen in FIG. 10, there may be a dense collection of particles of the lower right-hand corner of the screen which corresponds to highly effective blocking plotted against another parameter. FIG. 10 therefore demonstrates that highly pigmented particles have a very distinct signature in the (ALL) category. This signal may be used as an effective distinguishing signal to activate the fluid valve. Accordingly, in some embodiments, the target particles may be pigmented cells and wherein the loss of light is a result of absorption by pigmentation in the pigmented cells. The markerless signal may be axial light loss and the target particle may be a pigmented cell. In yet other embodiments, the target particle may be at least one of a pigmented cell, a stem cell, a cancer cell, a T-cell, a zygote, a component of blood, a protein, a DNA fragment, and a bacteria.

Figure 11:
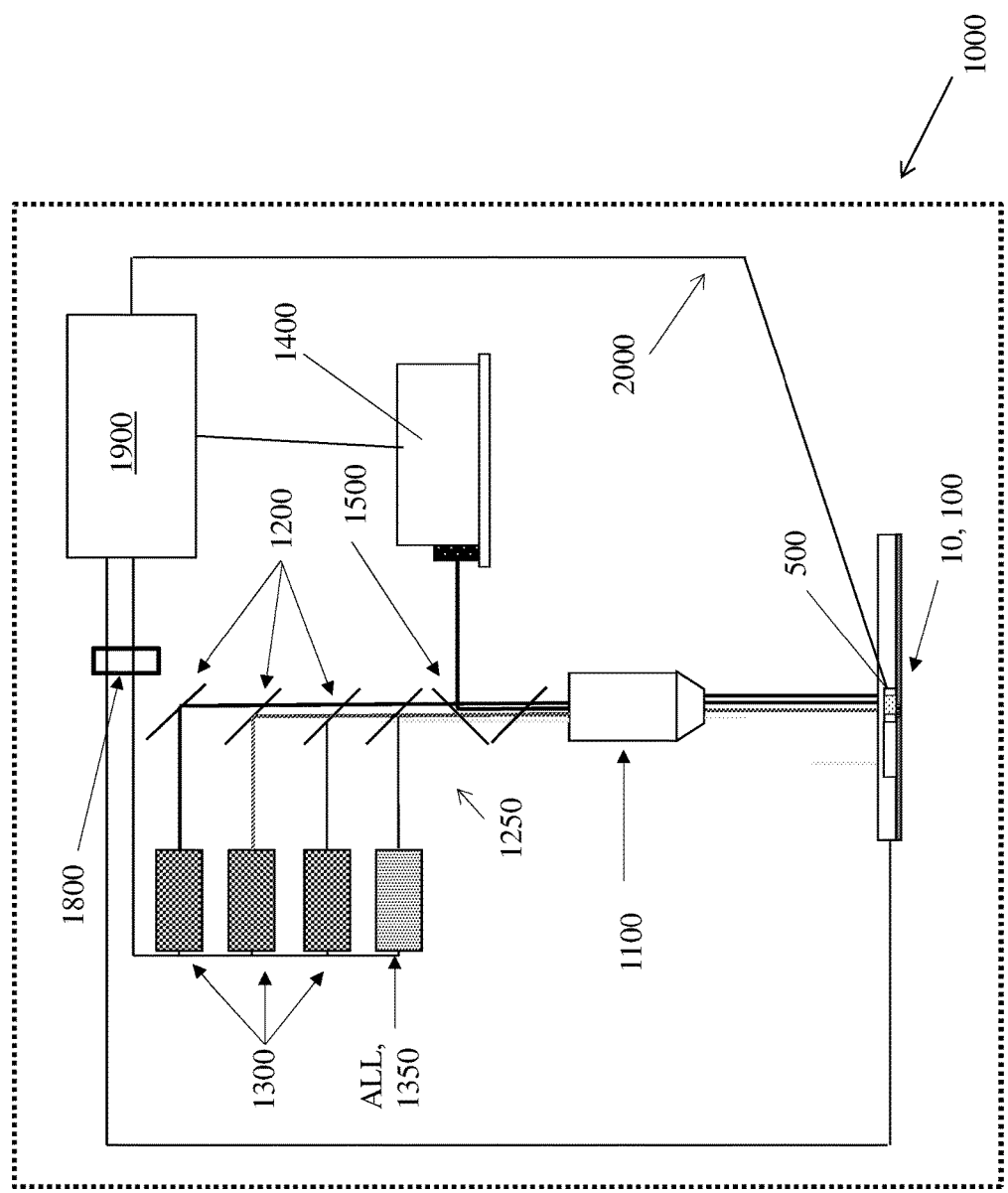
FIG. 11 is a system-level illustration of a microfabricated particle sorting system according to the present invention, showing the placement of the various detection and control components.

The microfabricated particle manipulation device or particle sorting device 10 or 100 may be used in a particle sorting system 1000 enclosed in a housing containing the components shown in FIG. 11. The MEMS particle manipulation devices 10, 100 or 800 may be enclosed in a plastic, disposable cartridge which is inserted into the system 1000. The insertion area may be a movable stage with mechanisms available for fine positioning of the particle manipulation device 10, 100 or 800 and associated microfluidic channels against one or more data, which orient and position the detection region and particle manipulation device 10, 100 or 800 with respect to the collection optics 1100. If finer positioning is required, the inlet stage may also be a translation stage, which adjusts the positioning based on observation of the location of the movable member 110 relative to a datum.

It should be understood that although FIG. 11 shows a particle sorting system 1000 which uses a single laser source 1400, it should be understood that multiple light sources, multiple detection optics and multiple channels may also be used.

The embodiment shown in FIG. 11 is based on a FACS-type detection mechanism, wherein one or more lasers 1400 impinges on the sample inlet channel 120 as described above. The relative amount of light lost may be monitored by a computer 1900. The computer 1900 may then generate a control signal that controls the electromagnet 500.

Accordingly, the MEMS particle sorting system 1000 shown in FIG. 11 may include a number of elements that may be helpful in implementing the detection scheme described above. A background light level may be measured and established by averaging over some period, to smooth out light fluctuations, reflections, etc. The sample fluid is then admitted to the microchannels and the light level is monitored. When the relative loss of light exceeds a certain threshold, the computer 1900 directs the sorter 100 to divert the target particle into the sort channel 120.

The optical components may include a beamsplitter 1500 and multiple color detectors 1300. The beam splitter 1500 may reflect the incoming light from laser 1400 onto the MEMS sorter 100, and pass the outgoing light reflected from the rear surface of the channel 120 to the turning mirrors 1200 and on to detectors 1300.

The output of detectors 1300 may be analyzed to invert the ALL signal and compare to a threshold.

Other sorts of components may be included in electronic distinguishing means 1800 to separate the signals from multiple laser sources, for example. These components may include, for example, a signal filter, mixer, phase locked loop, multiplexer, trigger, or any other similar device that can separate or distinguish the signals. Component 1800 may also include a high pass and/or low pass electronic filter or the envelope detector. The multiple sets of signals from the electronic distinguishing means 1800 may be handled differently by the logic circuits 1900 in order to separate the signals.

The MEMS particle manipulation system 1000 may be used in conjunction with one or more additional downstream optical interrogation regions, wherein the additional interrogation regions are used to confirm the effectiveness or accuracy of a manipulation stage in manipulating a stream of particles. The downstream regions may use an additional laser or optical detector such as a camera. The downstream evaluation from interrogation region 280 past the sorting stage 100 and 200 may allow the operator to measure one event number (e.g. the captured event rate post-sort) divided by another event number (e.g. the initial event rate pre-sort) for individual particle types, and to feedback to adjust initial interrogation parameters (e.g. such as x, y, z position and also "open window" length in time) based on this ratio. This method may be used to optimize the yield or accuracy of the system 1000. Alternatively, the operator could measure the event rate post-sort of target cells, divided by total event rate post-sort feedback to adjust initial laser interrogation parameters such as x, y, z position and also "open window" length in time, in order to optimize the purity of the sorting system 1000. These sorting parameters may be adjusted by changing control signal 2000 which is sent by computer 1900 to electromagnet 500, or by changing the optical detection parameters or by changing the laser control signals, as shown in FIG. 11.

Accordingly, a particle manipulation system is envisioned which not only includes the particle sorting device 1 as previously described, but further includes at least one laser directed to a laser interrogation region disposed in the inlet channel, and at least one set of detection optics that detects the markerless effect from the target particle in the fluid. The particle sorting system may further include an electromagnet and a circuit that provides a control waveform to the electromagnet. The particle sorting system may also include at least one additional detector directed at a region in at least one of the output channels to configured to confirm results of a particle manipulation.

Using the particle sorting device 1 and particle sorting system 1000, a method of sorting or separating a target particle using a microfabricated particle manipulation device may be practiced. This method may include providing a fluid stream containing target particles and non-target material, flowing in a microfabricated channel, applying a beam of light to the channel from an optical light source, disposing the particle sorting device in the microfabricated channel, detecting a markerless effect as the target particle passes through beam of the light source to generate a sort signal with a detector and moving the microfabricated particle sorting valve to deflect the target particle from the fluid stream in response to the sort signal.

Additional steps may include energizing the source of magnetic flux when the sort signal is generated.

The method may use a markerless signal such as axial light loss to detect an epithelial stem cell. The optical light source and detector may be substantially parallel, and wherein the detector detect incident light reflected from a back wall of the channel. The microfabricated particle sorting valve in this system may comprise a microfabricated, movable member formed on the substrate, and having a first diverting surface, wherein the movable member moves from a first position to a second position in response to a force applied to the movable member, wherein the motion is substantially in a plane parallel to the surface of the substrate, a sample inlet channel formed in the substrate and through which a fluid flows, the fluid including at least one target particle and non-target material, wherein the flow in the sample inlet channel is substantially parallel to the surface, a plurality of output channels into which the microfabricated member diverts the fluid, and wherein the flow in at least one of the output channels is substantially orthogonal to the plane, and wherein at least one output channel is located directly below at least a portion of the microfabricated member over at least a portion of its motion.

The sorting valve may include a first permeable magnetic material inlaid in the movable member, a first stationary permeable magnetic feature disposed on the substrate; and a first source of magnetic flux external to the movable member and substrate on which the movable member is formed.

The description now turns to the fabrication of the devices shown in FIGS. 1-11. Fabrication may begin with the inlaid permeable features 116 and 130 formed in a first substrate. The substrate may be a single crystal silicon substrate, for example. To form these structures, depressions may be formed in these areas of the substrate surface by etching. First, photoresist may be deposited over the substrate surface and removed over the areas corresponding to 116 and 130. Then, the trenches may be formed by, for example, etching the substrate in potassium hydroxide (KOH) to form a suitable depression. A seed layer may be deposited conformally over the first substrate surface and patterned to provide the seed layer for plating NiFe into the trenches. The seed layer may be, for example, Ti/W or Cr/Au may then be deposited by sputtering, CVD or plasma deposition. This layer may be covered with photoresist and patterned according to the desired shape of the areas 116 and 130. Unwanted areas of photoresist and seed layer may then be removed by chemical etching. The permeable features may then be deposited over the patterned seed layer by sputtering, plasma deposition or electrochemical plating. It is known that permalloy (80% Ni and 20% Fe), for example, can readily be deposited by electroplating.

Alternatively, a liftoff method may be used to deposit a sheet of permeable material, most of which is then lifted off areas other than 116 and 130. Further details into the lithographic formation of inlaid, magnetically permeable materials may be found in, for example, U.S. Pat. No. 7,229,838. U.S. Pat. No. 7,229,838 is hereby incorporated by reference in its entirety. The substrate may then be planarized by chemical mechanical polishing (CMP), leaving a flat surface for the later bonding of a cover plate.

Having made the permeable features 116 and 130, the movable member or valve 110 and 810 may be formed. The surface may again be covered with photoresist and patterned to protect the inlaid permeable features 116 and 130. The inlet channel 120 and output channels 122 and relieved area 144 may be formed simultaneously with the movable member 110 and 810. With movable member 110, 810 and other areas whose topography is to be preserved covered with photoresist, the features 110, 810, 120, 122 and 144 may be formed by deep reactive ion etching (DRIE) for example.

To form the fluidic channels, a cover plate may be bonded to the surface of the substrate which was previously planarized for this purpose. The cover plate may be optically transparent to allow laser light to be applied to the particles in the fluid stream flowing in the inlet channel 120, and for fluorescence emitted by the fluorescent tags affixed to the particles to be detected by the optical detection system described above. A hole formed in this transparent material may form the waste channel 142. Alternatively, a waste channel 142 may be formed in a second substrate, such as a second silicon substrate, and bonded to the surface of the first substrate. Alternatively, output channel 142 may be formed on the opposite surface of the first substrate using a silicon-on-insulator (SOI) substrate, with waste channel 142 and orifice 140 formed in the handle layer and dielectric layer of the SOI substrate, and the movable feature formed in the device layer.

Additional details for carrying out this process outlined above are well known to those skilled in the art, or readily found in numerous lithographic processing references.

While various details have been described in conjunction with the exemplary implementations outlined above, various alternatives, modifications, variations, improvements, and/ or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A particle sorting device with light-signal based particle detection, comprising:
   a fluid stream containing target particles and non-target material, flowing in a microfabricated channel;
   an optical light source which emits a beam of light into the channel;
   a microfabricated particle sorting valve disposed in the channel;
   a detector which measures a markerless effect as the target particle passes through beam of the light source and emits a sort signal; and
   a computer that generates a trigger signal to open the microfabricated particle sorting valve to deflect the target particle from the fluid stream in response to the sort signal;
   wherein the microfabricated particle sorting valve comprises:
   a microfabricated, movable member formed on a substrate, and having a first diverting surface, wherein the movable member moves from a first position to a second position in response to a force applied to the movable member, wherein the motion is substantially in a plane parallel to the surface of the substrate;
   an sample inlet channel formed in the substrate and through which a fluid flows, the fluid including at least one target particle and non-target material, wherein the flow in the sample inlet channel is substantially parallel to the surface;
   a plurality of output channels into which the microfabricated member diverts the fluid, and wherein the flow in at least one of the output channels is substantially orthogonal to the plane, and wherein at least one output channel is located directly below at least a portion of the microfabricated member over at least a portion of its motion.

2. The particle sorting device of claim 1, wherein the markerless effect is axial light loss, a reduction in detected axial light due to the obscuring of the light by a passing particle.

3. The particle sorting device of claim 1, wherein the target particle comprises a pigmented cell.

4. The particle sorting system of claim 1, wherein the optical light source and detector are substantially parallel, and wherein incident light from the light source is reflected from a back wall of the channel, and wherein the reflected light is separated from incident light by a beamsplitting reflector.

5. The particle sorting device of claim 1, wherein the plurality of output channels of the microfabricated particle sorting valve comprises a sort channel and a waste channel, wherein flow in the sort channel is substantially antiparallel to flow in the sample inlet channel, and wherein flow in the waste channel is substantially orthogonal to flow in the sample inlet channel and the sort channel.

6. The particle sorting device of claim 1, wherein the microfabricated particle sorting valve comprises further comprises:
   a first permeable magnetic material inlaid in the movable member;
   a first stationary permeable magnetic feature disposed on the substrate; and
   a first source of magnetic flux external to the movable member and substrate on which the movable member is formed.

7. The particle sorting device of claim 6, wherein the movable member moves from the first position to the second position when the source of magnetic flux is activated.

8. The particle sorting device of claim 1, wherein target particles are pigmented cells and wherein the loss of light is a result of absorption by pigmentation in the pigmented cells.

9. The particle sorting device of claim 1, wherein the markerless signal is axial light loss and the target particle is a pigmented cell.

10. The particle sorting device of claim 1, wherein the target particle comprises at least one of a pigmented cell, a stem cell, a cancer cell, a T-cell, a zygote, a component of blood, a protein, a DNA fragment, and a bacteria.

11. A particle manipulation system, comprising:
   the particle sorting device of claim 1;
   at least one laser directed to a laser interrogation region disposed in the inlet channel; and
   at least one set of detection optics that detects the markerless effect from the target particle in the fluid.

12. The particle manipulation system of claim 10, further comprising:
   an electromagnet; and
   a circuit that provides a control waveform to the electromagnet.

13. The particle manipulation system of claim 12, further comprising:
   at least one additional detector directed at a region in at least one of the output channels to configured to confirm results of a particle manipulation.

* * * * *